US006852089B2

(12) United States Patent
Kloecker et al.

(10) Patent No.: US 6,852,089 B2
(45) Date of Patent: Feb. 8, 2005

(54) COMPRESSION GARMENT FOR SELECTIVE APPLICATION FOR TREATMENT OF LYMPHEDEMA AND RELATED ILLNESSES MANIFESTED AT VARIOUS LOCATIONS OF THE BODY

(75) Inventors: Richard J. Kloecker, County of St. Louis, MO (US); Kent F. Schien, County of Chesterfield, MO (US); James A. Muir, County of Ballwin, MO (US)

(73) Assignee: Innovative Medical Corporation, St. Louis, MO (US)

( * ) Notice: Subject to any disclaimer, the term of this patent is extended or adjusted under 35 U.S.C. 154(b) by 0 days.

(21) Appl. No.: 10/208,164

(22) Filed: Jul. 29, 2002

(65) Prior Publication Data

US 2004/0059274 A1 Mar. 25, 2004

Related U.S. Application Data

(63) Continuation-in-part of application No. 10/008,545, filed on Nov. 13, 2001, now Pat. No. 6,436,064, which is a continuation-in-part of application No. 09/559,682, filed on Apr. 27, 2000, now Pat. No. 6,315,745.
(60) Provisional application No. 60/131,697, filed on Apr. 30, 1999.

(51) Int. Cl.$^7$ .............................................. A61L 15/00
(52) U.S. Cl. ........................ 602/75; 602/13; 602/63; 602/901; 601/151; 601/152; 128/878
(58) Field of Search ................... 602/75, 76, 77, 602/13, 61, 62, 63, 67, 901, 23; 128/869, 878, 876, 882; 601/150, 151, 152, 134; 600/498; 374/4

(56) References Cited

U.S. PATENT DOCUMENTS 3,888,242 A * 6/1975 Harris et al. ............... 601/152
4,029,087 A * 6/1977 Dye et al. .................. 601/152
4,091,804 A * 5/1978 Hasty ........................ 601/152
4,150,442 A * 4/1979 Boone ......................... 602/63
4,186,738 A * 2/1980 Schleicher et al. ........... 602/23
4,207,876 A * 6/1980 Annis ........................ 601/152
4,256,094 A * 3/1981 Kapp et al. ................ 601/152
4,269,175 A * 5/1981 Dillon ....................... 601/152
4,369,588 A * 1/1983 Berguer ..................... 128/882
4,374,518 A * 2/1983 Villanueva ................. 601/152
4,396,010 A * 8/1983 Arkans ...................... 601/152
4,408,599 A * 10/1983 Mummert ................... 601/152
4,657,003 A * 4/1987 Wirtz ........................ 128/869
4,744,391 A * 5/1988 Lardner ..................... 600/498
4,998,582 A * 3/1991 Fudono et al. ................ 374/4
5,125,400 A * 6/1992 Johnson, Jr. ................. 602/13
5,179,941 A * 1/1993 Siemssen et al. ........... 601/152
RE34,661 E * 7/1994 Grim .......................... 602/13
5,328,445 A * 7/1994 Spahn et al. ................. 602/13
5,437,610 A * 8/1995 Cariapa et al. ............. 601/152
5,443,440 A * 8/1995 Tumey et al. .............. 601/152
5,450,858 A * 9/1995 Zablotsky et al. ......... 128/876
5,575,762 A * 11/1996 Peeler et al. ............... 601/152
5,591,200 A * 1/1997 Cone et al. ................. 601/152
5,626,556 A * 5/1997 Tobler et al. ............... 601/151
5,916,183 A * 6/1999 Reid .......................... 601/134

* cited by examiner

Primary Examiner—Fadi H. Dahbour
(74) Attorney, Agent, or Firm—Paul M. Denk (57) ABSTRACT

A compression garment for selective application for treatment of lymphedema and related illnesses manifested at various locations of the body. The garment includes a pair or series of layers of hermetically sealed material, that can capture pressurized air, when applied therein, and is formed through the patterned sealing of the layers of the garment together, at select locations, to form air pockets that can selectively apply isolated points of pressure to the patient's affected area, without disrupting normal vascular and lymphatic functioning. The garment is design cut, for application to various segments of the body, and applies encompassing pressure over the entire affected area, and includes valves that can allow for the injection of measurable air, to the desired pressure points, or its deflation, after treatment.

15 Claims, 9 Drawing Sheets

COMPRESSION GARMENT FOR SELECTIVE APPLICATION FOR TREATMENT OF LYMPHEDEMA AND RELATED ILLNESSES MANIFESTED AT VARIOUS LOCATIONS OF THE BODY

CROSS REFERENCE TO RELATED APPLICATION

This application is related to and comprises a continuation in part of the U.S. patent application of the same inventor, Ser. No. 10/008,545, filed on Nov. 13, 2001 now U.S. Pat. No. 6,436,064, which is a continuation in part of the U.S. patent application Ser. No. 09/559,682, filed on Apr. 27, 2000 now U.S. Pat. No. 6,315,745; said previous application being related to its provisional application having Ser. No. 60/131,697, filed on Apr. 30, 1999, all of said applications being owned by the same inventor.

STATEMENT REGARDING FEDERALLY SPONSORED RESEARCH OR DEVELOPMENT

N/A

BACKGROUND OF THE INVENTION

This invention relates primarily to the treatment of lymphedema, and the use of various instrumentation that can effectively lessen the painful and deleterious aspects of such disease as manifested in the body.

As is well known in the art, lymphedema is a collection of fluids within the tissue, usually extremities, such as one or both of the arms, one or both of the legs, and which is caused from various etiological causes. Lymphedema can be a primary illness that is congenital. This can either result from aplasia of the lymphatic system, which may occur as a result of a complete lack of development of the same, or can be caused by hypoplasia of the lymphatics, such as an underdevelopment of the lymphatic system. Furthermore, lymphedema can be caused, and result from inflammatory diseases. These include mostly bacteriological infections. The non-infectious inflammatory causes are due to a variety of impairments, such as malignancies where the lymphatics can be blocked by tumor cells, or the lymph nodes can be blocked by tumor cells. In addition, it can result from the surgical removal of various lymph nodes, and the surgical interruption of the normal performance of the lymphatics. Furthermore, such can come from radiation that causes sclerosis or scarring of the lymphatics. Furthermore, such can result from chronic venous diseases of long standing origin. In addition, lymphedema can come from severe local injury to a limb. Furthermore, it is usually the infectious element that accompanies such an injury that may result in the onset of lymphedema. Lymphedema can also originate from the blockage of lymphatics by various parasites. Finally, pathology in lymphatics can come from various systemic diseases including myxedema, renal disease, such as nephritis or nephrosis, with loss of protein materials, and can derive from various collagen diseases and fibrotic diseases. All of these diseases result in obstruction of the lymphatic flow and thus causes an accumulation of fluids in the effected limb or limbs. It is also known that cardiac failure can also cause the onset of this malady.

Until recent years, the lymphatic system's anatomy has only been demonstrated in its larger or more gross form. Millions of small lymphatic ducts have not been truly understood or demonstrated until the past several years, and only as a result of extensive research. The smaller lymphatics, which were cannulated under the magnification of the electron microscope, have been demonstrated as playing a role in the onset of this type of disease. Such had been predicted for a number of years, but it was not demonstrated until approximately two years ago. Now, the network of the lymphatic system is fairly well understood and known. The lymph system is actually inherent in all of the bodily organs, but the major part of the lymphatic system in the extremities is in the subcutaneous tissues. Such has been demonstrated.

The effects of lymphedema on the patient are well known. Patients generally are somewhat or significantly disabled according to the limb that is affected. Usually, with the onset of lymphedema, the patient either has one or two lower limbs that are very heavily affected, and manifest a heavy accumulation of such body fluids. As the disease progresses, it hampers the patient's ambulation and makes it very difficult for normal clothing to fit. Eventually, normal everyday activities become limited. If lymphedema effects the upper extremity, the hand is markedly affected, and the mobility of the hand, fingers and thumb, etc., are eventually also affected. In addition, these people, subject to lymphedema, are very susceptible to various other serious infections. A very slight portal of entry, such as a cut, pin stick, hangnail, or the like, or anything that allows the entrance of bacteria into the lymphatic system becomes a very serious cellulitic process. This can reach proportions of fever and chills, and even require hospitalization, and if uncontrolled can even cause septic shock and death. The reason for this is that the lymph fluid is a perfect media for bacteria to grow in and there is an abundance of such fluid in those subcutaneous tissues.

Lymphedema is commonly seen in either the upper or lower extremities of the body as mentioned above. This can be either individually, or isolated in its location, depending upon where the lymph nodes have been removed, or it can manifest itself in a variety of these extremities, after its onset. Some of the cases of lymphedema are normally due to chronic venous disease. However, the largest number of such cases have been caused by secondary reactions to radiation and radical surgery where either all of the lymph nodes were removed from a groin area, the pelvis, or from an axilla. There was no real algorithm of treatment until the late 1980's.

Currently, literature has become more proliferative on the problems associated with lymphedema. Studies, even by the inventor herein, have focused more attention to lymphedema, and have led to an extrapolation of some hypothesis as to its etiology at the level of the microscopic lymphatics.

There are a variety of treatments that are currently available for lymphedema, and most of them, relate to some type of wrapping or compression of the effected area, in an effort to reduce the accumulation of the fluids. Many of the processes have included various types of wraps, or pumps, for achieving a dissemination of the localized fluids.

For example, the Reid sleeve is one such instrument that has been used for the treatment of lymphedema. It is a sleeve type compression device, almost in the nature of a cast, but in this instance, formed of more flexible type of nylon or related materials. Then, a series of straps can be tightened around the sleeve, at the situs of the accumulated fluids, and tightened by means of any type of fastener associated with such straps, in order to apply compression at the site of treatment. Thus, the essence of the Reid sleeve is simply to provide a massive amount of physical pressure by tightening of a sleeve about the infected area.

The use of such compression bandaging has provided some beneficial results to the patient, and has achieved limb reduction, enhanced skin tone, and softer skin texture, but, the use of such a bandage does have the potentially harmful effects of functioning like a tourniquet upon the effected area, and unless the amount of pressure applied is significantly controlled, can have further detrimental effects in the nature of reducing blood circulation and flowage, which can be very harmful to the patient, if not properly supervised. Most of these sleeve type of devices, available in the art, may be initially applied by the medical practitioner, in the office, but once the patient takes it home, he/she will either be advised or have a tendency to apply such sleeves themselves, which can afford no regulation over the amount of pressure applied by such a compression sleeve, once installed.

It has also been suggested, recently, that some type of air compressive means or strap may extend, at a slight width, along the internal length of the Reid or related sleeves, and be pumped up to provide additional tightness to the device encompassing the limb. But, once again, such applications offer little or no control over the amount of pressure applied, or the benefits or harm that may result from their usage, particularly when applied by the patient alone.

Various United States patents have previously issued relating to technology available for treatment of accumulation of body fluids, or for other treatments. For example, in the U.S. Pat. No. 4,029,087, entitled "Extremity Compression Device," there is shown, as can be seen in its FIG. 1, a wrap that applies compressive pressures against the patient's limb, forming interconnecting annuluses, as noted, and which are inflated. Generally, this particular compression device is for application to patients that are bedridden, for some time, and with the added pressure it is believed that assistance to blood flow may be enhanced, to reduce swellings associated with edema in the extremities.

The compressive sleeve to Hasty, shown in U.S. Pat. No. 4,091,804, shows a form of sleeve that is applied to the patient's limb, and subjects the same to compressive pressure, as a result of the injecting of compressive air into the various chambers, as noted, to provide compressive pressures against the patient's limb.

The patent to Annis, U.S. Pat. No. 4,207,876, shows a compression device with ventilated sleeve. This device may be applied, as for example, to the leg of a patient, to apply compressive pressures, during treatment. This device includes various openings to provide ventilation to the limb, during the application of this compression device, when used for treatment.

The patent to Kapp, et al, U.S. Pat. No. 4,256,094, shows an arterial pressure control system. This device utilizes a fluid pump for inflating a cuff, which functions, apparently, to provide arterial pressure, not too unlike that of the manual tourniquet.

The patent to Dillon, U.S. Pat. No. 4,269,175, discloses an apparatus that promotes the circulation of blood. This particular device, when applied, as for example, to the leg, and fluid pressure is injected into the same, as can be seen in its FIG. 1, is designed to enhance or provide intermittent external pressure pulses to the leg, to enhance blood flow, to and from the heart.

The patent to Villanueva, U.S. Pat. No. 4,374,518, shows an electronic device for pneumomassage to reduce lymphedema. This device includes the fabrication of an outer boot, that may fit, for example, to conform to the human foot and leg, and utilizes a compressor to provide for successive inflating and deflating of the boot, within a preselected cycle, in order to stimulate fluid flow.

The patent to Arkans, U.S. Pat. No. 4,396,010, shows a sequential compression device. This device, as with those as previously described, is a pressure generating device for applying compressive pressures from a compressor against the patient's limb, through the use of a flexible, prepressurizable sleeve that encloses the limb and apparently pulsates pressure to the sleeve, and on to the limb, to enhance fluid flow.

The patent to Mummert, U.S. Pat. No. 4,408,599, discloses another complex apparatus for pneumatically controlling a dynamic pressure wave device. This device includes a series of longitudinal chambers that are subject to pressure inflation or deflation, by a dynamic pressure generating device, which is highly controlled by means of electrically operated components.

The patent to Siemssen, et al, U.S. Pat. No. 5,179,941, shows a contractile sleeve element and compression sleeve made therefrom for the peristaltic treatment of extremities.

The patent to Cariapa, et al, U.S. Pat. No. 5,437,610 shows another complex device incorporating various compression units, and pump means, which functions as an extremity pump apparatus.

The patent to Tumey, et al, U.S. Pat. No. 5,443,440, shows another form of medical pumping apparatus, in this particular instance, for application to the foot, and which can be inflated, in order to apply pressure to the foot, during its treatment for various impairment.

The patent to Peeler, et al, U.S. Pat. No. 5,575,762, shows a gradient sequential compression system and method for reducing the occurrence of deep vane thrombosis. This is a complex apparatus, for treatment as a therapeutic medical device and method for improving the venous blood flow within the patient.

The patent to Cone, et al, U.S. Pat. No. 5,591,200, shows another method and apparatus for applying pressure to a body limb for treatment of edema. This device is similar to the Reid sleeve, as previously reviewed.

Finally, the patent to Tobler, et al, U.S. Pat. No. 5,626,556, discloses a hook and loop attachment on a compression sleeve. This particular device also is related to the Reid sleeve type of apparatus, as previously explained, and does provide for the application of air pressure, into the lateral annuluses, as shown; to provide an inflated pressure against the foot, as can be noted, for the treatment of the patient's leg, and perhaps other extremities.

SUMMARY OF THE INVENTION

This invention relates generally to a portable form of compressive garment that may be selectively applied to various extremities of the body to provide for treatment of lymphedema and related forms of edema.

Figure 1:
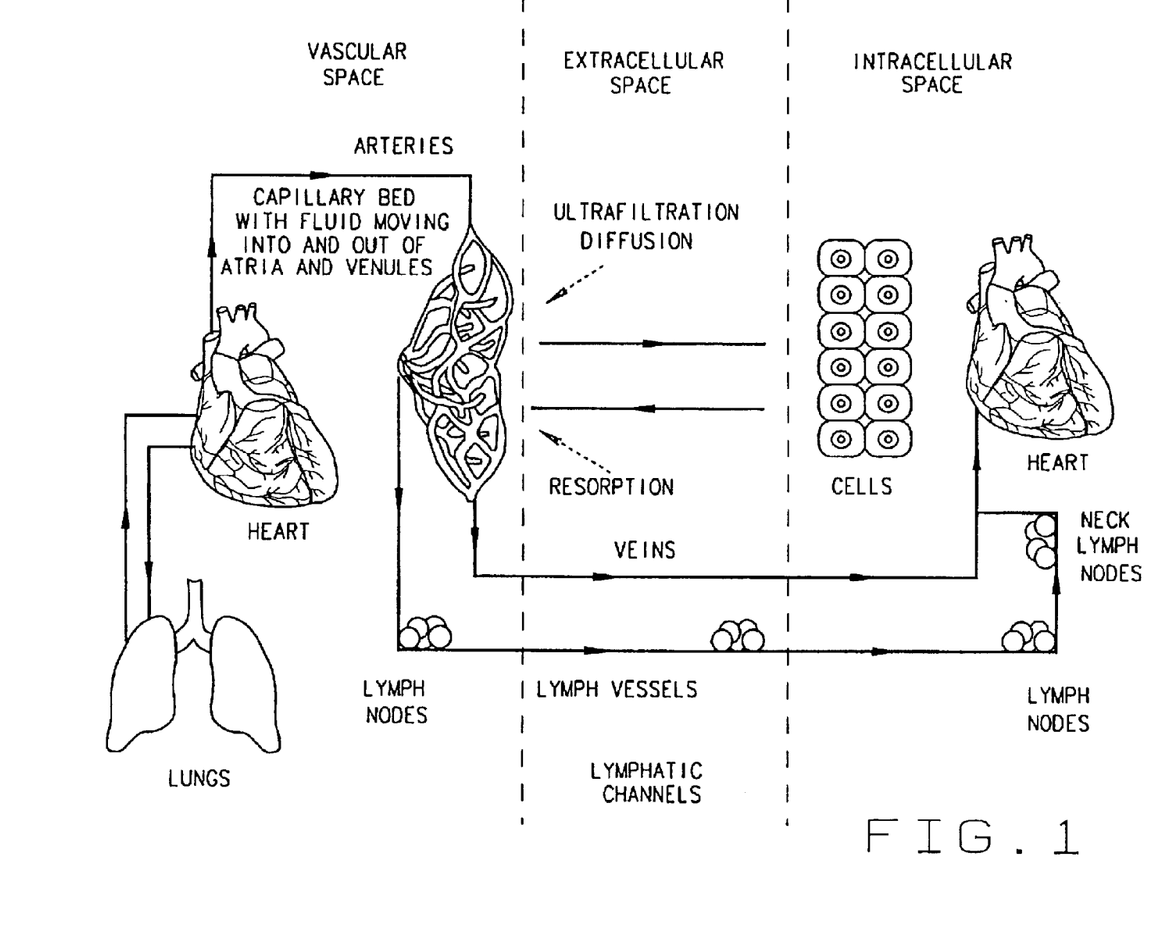

The lymphatic system of the body is actually a part of the human closed hydraulic system of circulation within the anatomy, that provides for sustaining normal physical function of the body parts, provides the proper displacement and movement of the various fluids, separate and apart from the circulation of blood within the body. As can be seen in FIG. 1, the location and functionality of the heart, lungs, the arteries, veins, and the other circulatory and vascular system of the body is compatibly associated with the extracellular lymphatic space. These lymphatic channels provide for transportation of lymph fluids to lymph nodes that remove various materials such bacteria and debris. Finally, the lymph fluid is discharged into the veins by way of the thoracic duct. Thus, this portion of the vascular system combats disease, by carrying away the deleterious bacteria and other infections elements that can cause problems to the body. In this FIG. 1, blood flowing into the small vessels (arterioles) entering the capillaries at that level, delivers nutrition to the intracellar spaces by ultrafiltration.

After depositing nutrients to the cells, the fluid traverses the extracellular space and is resorped in the venous end of the capillaries. However, only 90% enters the venous plexus and 10% flows into the lymphatics. The latter is profused through the lymph node basins (inguinal, axillary, intra abdominal and supraclavicular) and returned to the large veins at the left thoracic inlet via the thoracic duct. Thus, the fluid exchange that contributes to lymph formation originates at the microscopic level and is governed by Starlings laws of capillary function.

The subject matter of this current invention contemplates the formation of a compression garment that is selectively designed and manufactured to provide for application by the patient himself/herself. Once instructed, in proper placement it furnishes greater and more precise control, for treatment of the deleterious side effects manifested by and through lymphedema, as explained. In essence, the subject matter of this invention provides for the formation of an external compression device that may be applied to the arm, and embrace even part of the hand, or even extend upwardly into the region of the shoulder. Or, the sleeve may be especially designed for application to the leg, and extend down into the region of the ankle, and even embrace part of the foot, and extend upwardly towards the knee and thigh, depending upon the severity of the lymphedema being treated, and its location. Thirdly, the invention contemplates the formation of a further wrap, fabricated to the same principle as that of the previously identified sleeves, and which may embrace the upper thighs, and the lower abdomen, in order to provide the precise application of select pressure to the accumulation of body fluids, caused by lymphedema, manifested at these regions of the body. Adaptation for the thorax is also a possible option.

In essence, the appliance of this invention is formed as a flexible cloth, polymer, or related type of material, that has a series of grommets or seal points that form individual and smaller pressure chamber segments internally of the overall formed device. As grommets, placed 3 cm apart, provide for venting, from between the skin surface and the device, once installed.

In addition, there are one or more inflation or deflation valves, operatively associated with the internally formed compartments for the device, and in addition, the selective emplacement of the grommets, during formation of the device, furnish subsidiary chambers throughout the length of the formed device, so that multiple pressure points may be generated, within the inflated device, to apply multiple sites of pressure to the lymphedema that is subject to treatment. This strategic placement affects capillary pressures. The device is custom made, so that it may precisely fit not only upon the arm, leg, or the like, but has appendages that allow for the selective application of the device, for example, around the hand, under the thumb, so as to provide adequate coverage to all aspects of the limb subject to treatment, and afford a uniform application of pressure, through its various and multiple pressure points, to provide for a displacement of the edematous fluids, and their movement back into the circulatory system, in association with the adjacent lymphatic nodes, lymph vessels, and shifting of such fluids throughout the lymphatic channels, to reduce the undesired and frequently painful fluid accumulations.

In the formation of the device, at least a pair of layers of sturdy but flexible material, such as nylon, or other material that can be fabricated to provide for its inflatability, remain hermetically sealed, and be subject to significant pressures, while sustaining inflation, in order to function as an instrument for treatment of lymphedema, as previously explained. The precise location of the grommets, used to contiguously adhere the layers, at particular sites, but to allow for its inflatability, so as to form essentially three-dimensional diamond shaped pressure points. This allows increased venous flow by decreasing arteriolar hydrostatic pressure at these pressure points. These grommets, approximately three centimeters apart, more or less, afford a multiplicity of pressure points, upon the surface of the skin, thus reducing the lymphedema fluid, during usage. Obviously, other dimensions for placement of the seal points, or grommets, may be considered, depending upon the degree of lymphedema being treated, and it is likely that the grommets may be located approximately one inch apart, or as much as five inches apart, depending upon the degree of pressure required, to sustain a uniform pressure over the entire surface being treated.

In addition, there are various inflation or deflation valves that may be added to the device, to allow for its inflation, and there may be a single valve, or perhaps valves that may locate approximately two to four inches apart, to allow for isolated injection of air into the device, during its inflation, once placed on the limb. The patient himself/herself may actually apply the device, by wrapping it, as an example, about the arm, and the hand, and secure the same in the position by means of any type of straps, such as Velcro hook and pile type tab connections, that may extend along the marginal edge of the device, and cooperate with a velour surface applied externally to the device, to furnish securement. Or, a series of Velcro or other buckle straps may locate along the margins of the device, and allow for a strap fastener of the wrap, about the arm, leg, or the like, once installed.

Any type of a pressure applying and generating device may be used, for inflating the device, such as a bulb type hand pumping and fitting means, of the type that is available from Haikey-Roberts Company, of St. Petersburg, Fla., and which is shown in its U.S. Pat. Nos. 4,744,391 and No. 4,998,582. These hand pumps, that incorporate their own fittings, may be pumped for injecting pressurized air into an encapsulated space, in order to inflate the same, or its opposite end incorporates a fitting that may be inserted into the inflation-deflation valves, to allow for a deflating of the device, after its usage. Other bellows type air inflating device may be used. Normally, the amount of pressure that is applied in the device of this type, and which has been found effective, is in the range of 35–45 mmHg, more or less.

Thus, the amount of pressure applied is not too great, when it is compared with the amount of pressure that exists in the normal vascular system of the body, where a blood pressure may extend between diastolic and systolic ranges between 70–80 mmHg and 110–120 mmHg. On the other hand, the amount of pressure applied into this device, by means of a pressurized air injecting means, such as the bulb as previously explained, may be between the ranges of 5–10 mmHg, and upwards of 20–25 mmHg, or even as high as 40–50 mmHg, depending upon the amount of treatment required, and the form and extent of edema that may be present due to the magnitude of the lymphedema that exists.

Various other types of valves may be included in the structure of this garment, within each segment of its formed multi-compartment wrap, so that each segment may be individually filled with air, under pressure, to the amounts as previously reviewed, necessary to treat the degree of lymphedema that has been generated within the limb at that contiguous location. For example, various types of shut-off valves, one-way check valves, and valves that may be manually opened, to provide for release of pressurized air, are readily available from a variety of sources. For example, Colder Products Company, of St. Paul, Minn. 55114, manufactures and markets a variety of various types of valves, check valves, release valves, and couplings, for use for the application and release of air, under pressure, to medical instruments. In addition, the Martin-Weston Company, of Largo, Fla. 33770, manufactures and markets inflation pumps that may be applied to the foregoing type valves, to allow for the injection of air under pressure into the segments of this garment, during its installation and usage. On the other hand, instead of utilizing a manual type of pump, there are many more expensive type of pumps, valves, seals, and the like, that are available from a variety of sources, such as the fill and drain closures that are available from a company such as Halkey-Roberts Corporation, of St. Petersburg, Fla.

Furthermore, in order to determine the degree and amount of pressure applied into each segment of this garment, hand-held type of digital manometers may be used, and applied to the valves after or during the injection of air, to provide for an immediate digital readout of the amount of pressurized air that has been applied into each segment of the garment, so that more precise levels of pressure can be generated, at select locations along the length of the garment, as applied to a limb. Such hand-held manometers are available from Dwyer Instruments, Inc., of Michigan City, Ind. 46361, amongst other and a variety of sources.

In addition, in lieu of the use of a manometer, attached to the valves or to the segments of this wrap, it is just as likely that a form of pressure transducer may be utilized within each segment of the wrap, detect the amount of pressure generated therein, convert it to a charge, and transfer it to a readout, upon the surface of the segment, where the generated pressure may be readily observed. Such transducers may be obtained from Linton Instrumentation, of Diss, Norfolk, U.K., under Model No. SensoNor 840. For example, an LED readout that may display the quantity of pressure generated could be provided upon the surface of each segment, to let the physician and medical technician know the exact amount of pressure generated within each segment, during usage and application of the wrap. Also, if the patient utilizes the garment at home, through self service, this would provide a ready readout as to the amount of pressure pumped into each segment, during usage and application, so the patient may be quite precise in the amount of pressure developed within the wrap, in accordance with the specifications from the doctor, instructing regarding its usage. Furthermore, the pressure transducers may be incorporated into the inner surface of the wrap, or applied upon that surface of the wrap that is applied directly to the affected limb, so that an exact reading of the amount of pressure generated upon the surface of the limb subject to lymphedema, may be readily determined, upon usage of this particular garment.

Obviously, the type of material used as previously referred to in forming the multi-layer device, that exhibits the internal chambers that are fabricated to provide for the multipressure points from the device, when used, and may include those materials as previously described, while the internal surfaces of the liner may be treated, to make it hermetically sealable, or it may include an internal liner of a polymer, such as polyethylene, to assure that the device, during usage, will be pneumatically leak proof.

In addition, and in the case of the device as manufactured for use upon the arm, it may extend and wrap around the palm, leave clearance for the fingers and thumb. It may provide integral wrapping about the wrist, forearm, elbow, biceps, and even extend up into the region of the shoulder. Or, the device can be formed of a shorter dimension, depending upon the localized need for treatment. In addition, it may be formed for wrapping about the leg, the thigh, down to the ankle, and even about a portion or all of the foot, depending upon the severity of the lymphedema, and the type of treatment required. And, as previously explained, the device may be fabricated for wrapping about the lower abdomen, and have a connecting portion that may wrap about, individually, each of the upper associated thighs, to provide a localized treatment at that region of the body, which can frequently manifest lymphedema that requires treatment as such swelling may result from radical surgery that is done for cancers in the pelvic organs, such as the uterus, ovaries, rectum and prostate. Radiation of this region can also cause sclerosis of lymphatics resulting in edema.

It is, therefore, an object of this invention to provide an appliance for use for treatment of lymphedema that is light weight, very portable, washable, and easily applied, even by the patient alone.

Another object of this invention is to provide a lymphedema treating device that includes a series of perforations, at the region of grommets, or seals, which provides two beneficial results. One, which allows the access of air to the underlying and wrapped skin during usage of the device, but secondly, includes a series of seals, at these locations, which afford the generation of air pockets. This series of grommets produce a multitude of pressure points internally along the entire length and circumference of the applied sleeve rendering variable pressure on the capillary beds.

A further object of this invention is to provide a pressure garment that allows for its generated pressures, internally, during usage, to be precisely controlled, even by the patient during application and usage. LED pressure sensors provide this information.

Still another object of this invention is to provide a much less costly type of appliance, for treating lymphedema, than currently in use.

Still another object of this invention is to provide a pressure garment that incorporates at least two fail-safe features, one is in a valve or valves that allows filling only a certain pressure, and/or an appliance that fills the air chambers that only allows a maximum pressure of up to 45 mm of mercury, or slightly there above, and certainly below such level as could be harmful.

Still another object of this invention is to provide for a pressure garment for use for treating lymphedema that is easily and quickly applied to the effected limb.

Yet another object of this invention is to provide a pressure garment that is durable.

Still another object of this invention is to provide a device for treating lymphedema which is very compact, as during nonusage, and is very accommodatable for travel, when required.

Another object of this invention is to provide a very simple design that is safe in its application, installation, and usage.

Yet another object of this invention is to provide a pressure garment which when applied can aid towards decreasing post-operative edema and thus decrease post-operative disability and enhance the healing of a wound.

Another object of this invention is to provide a lymphedema treating device that may facilitate and be of help to the patient after orthopedic surgery, any surgery, or even during post-operative vascular surgery healing in the extremities.

Yet another object of this invention is to provide a somewhat flexible, inflatable edema treating device that will further act as a support that may even function somewhat as a cast to limit the amount of flexion of a limb, but yet, have sufficient flexibility to allow the limb to attain some movement, during usage.

Another object of this invention is to provide a garment for use for treating lymphedema that may be manifested, usually after surgery, in various limbs of the body, such as along the arms, in the lower reaches of the legs, at the thighs, or even in the vicinity of the abdomen, and unless treated, results in a buildup of significant accumulation of bodily fluids that are unsightly of appearance, but more specifically, detrimental to the continuing health or recovery rate of the patient. A body wrap may be beneficial in burn treatment also.

These and other objects may become more apparent to those skilled in the art upon reviewing the summary of this invention, and upon undertaking a study of the description of its preferred embodiment, in view of the drawings.

BRIEF DESCRIPTION OF THE DRAWINGS

In referring to the drawings, FIG. 1 provides a schematic view of the human closed hydraulic system of circulation of both vascular and lymphatic fluids depicting the formation of lymphatic fluid in the extracellular space.

DESCRIPTION OF THE PREFERRED EMBODIMENT

Figure 2A:
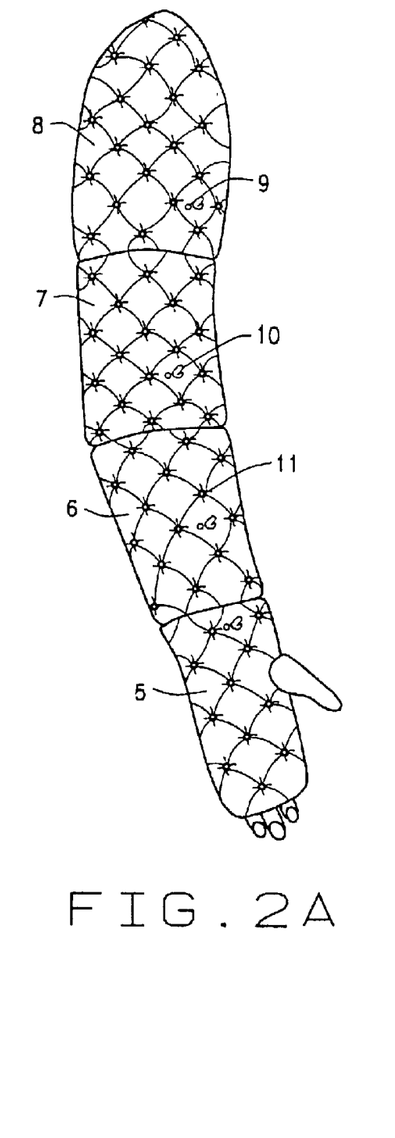
FIG. 2 provides a perspective view, both in the lateral view, and the medial view, of the compression garment of this invention applied about the lower arm and hand of the patient.
Figure 2B:
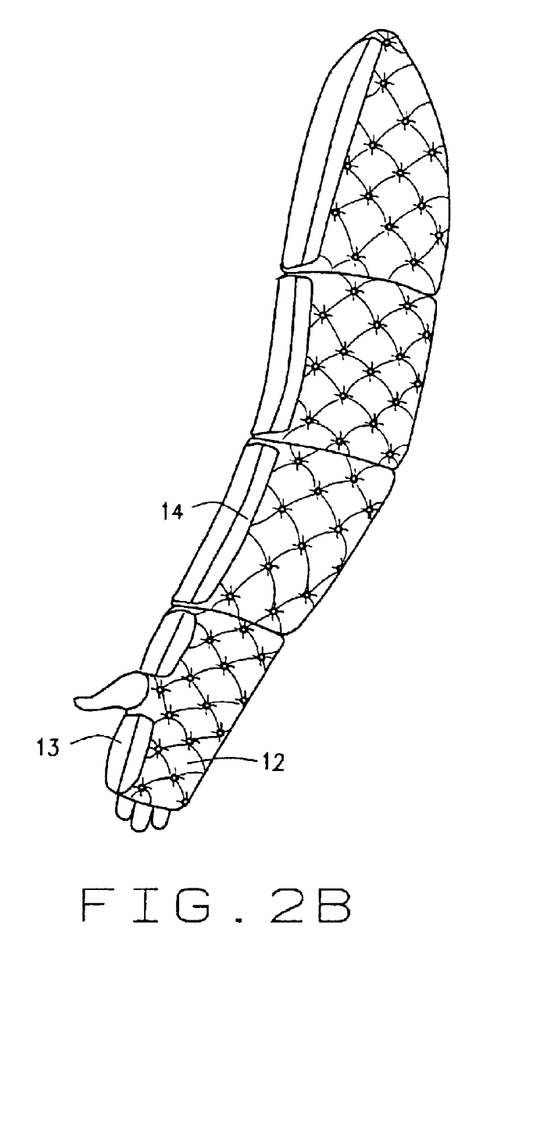
Figure 3:
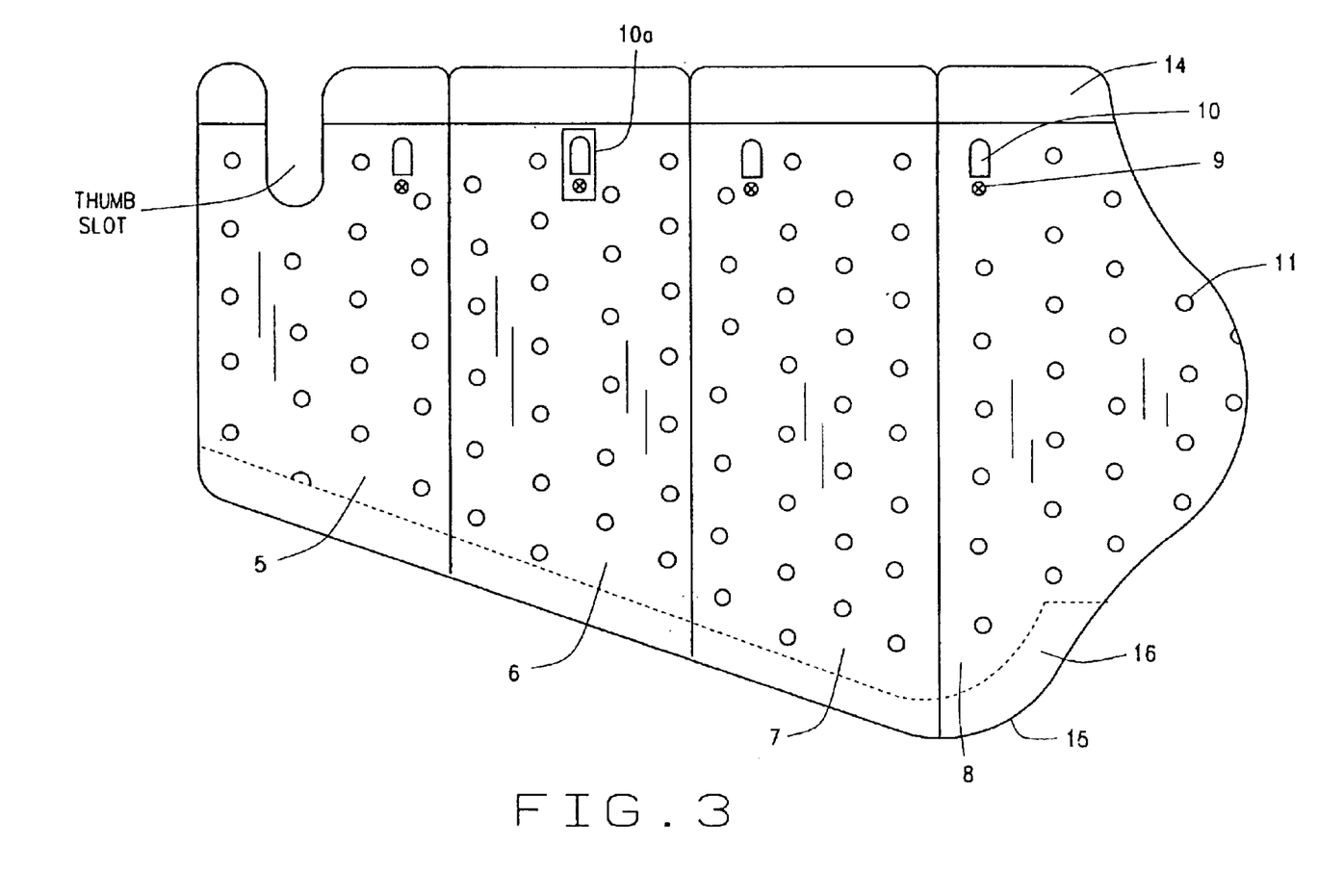
FIG. 3 is a plan view of the compression garment, during nonusage, as shown in FIG. 2.
Figure 4:
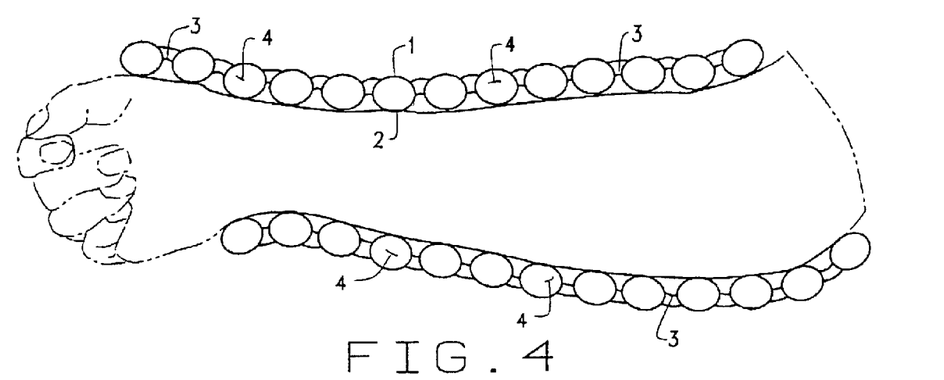
FIG. 4 is a sectional view of the arm applied garment, taken along the line 4—4 of FIG. 2.

In referring to the drawings, and in particular FIGS. 2 through 4, the compression garment G of this invention is readily disclosed. In this embodiment, it is applied to the forearm, about the wrist, and embraces part of the hand of the wearer or patient. The garment, as can be noted in FIG. 3, comprises and is formed of a flattened configuration, including upper and lower layers 1 and 2 of a fabric-like material, such as nylon, or any other hermetically sealable type of cloth, polymer, or flexible material, and which can be inflated to sustain pressures of air or other fluids to the amounts as previously summarized. As can be seen, the two layers of material are sealed together, by means of a series of grommets 3 throughout their extent, and which provide for segmented pockets, as at 4, of air that provide for a generation of point pressures, to the treated arm, as previously explained. The object for forming these various air pockets, along the length of the compression garment, and as previously summarized, is to provide the application of a very controlled pressure, at spaced and isolated locations, to the edema effected limb. At the same time avoiding the application of tourniquet type pressure, throughout the extent of the limb to which the garment is applied, so as to not curtail or shut off the vascular functioning in the effected area. Thus, blood flow in subcutaneous and fluid migration, during he application of the device's controlled pressure, will cause accumulated fluids to continue their circulation, but reduce their accumulation, to attempt to place the affected limb back into its normal processing, normal appearance, and to avoid the deleterious and impairments that may be generated in the limbs, because of the accumulation of the edemic fluids.

The compression garment may be a continuous length of the material, and liners, forming the length of the garment, and be inflated between its various grommets to form the identified pressurized air pockets, or as shown in FIGS. 2 and 3.

The garment may be segmented, between the various segments 5 through 8, and be individually inflated, by means of their respective valves (10), as can be noted. These valves (10) are provided for both inflating of the garment, or its individual segments, or it can be used for discharging and deflation of air, for either greater proper control of the amount of pressure applied, or for removal of the garment, after treatment.

In addition, the various grommets 3, as can be seen, have apertures, as at 11, within their interior, so as to allow for any captured air, between the garment and the surface of the limb skin, to escape, and which would otherwise, or may, provide a variation in the amount of pressure desired, when inflating the garment during usage.

As can also be seen, various types of sensors, as at 9, may be installed into the layers forming the surface of the garment, and be sensitive to the amount of pressure being added into the various segments, to provide a ready indication and readout of the amount of pressure applied, so the medical practitioner, or even the patient alone, can readily determine whether adequate and proper pressure levels have been reached, during treatment. Furthermore, various types of microchips, or LED indicators, may be associated with the sensors, and provide a digital, or either analog, readout of the amount of pressure generated within the garment, and its various segments, during usage and application.

In order to provide for the uniformity for the product, and to add to its appearance, it is likely that a covering sheet, such as one shown by way of example at 10A, of the same or different material from which the segments of the wrap are formed, may overlap each of the valves 10 and sensors 9, so as to form means for covering these elements, during usage of the wrap. One edge of the cover may include a hook and pile fastener type of connector, so that the cover may be secured in place, once installed, or pulled free, to expose the valve or sensor, accordingly. See FIG. 3.

Structural wise, the garment, being previously described as being fabricated of at least a pair of layers, will extend the length of the limb to which it is applied, and as shown in FIG. 2, in that embodiment, extends up to approximately the elbow of the wearer. At its opposite end, the garment may be designed and fabricated, to include sufficient length to override most of the hand, up to the position of the fingers, including a segment at its opposite width, as at 12, which may embrace the palm of the hand, and cooperate with an appendage, as at 13, that extends down across the hand, between the index finger and the thumb, and for connection to the portion 13 of the shown garment. Furthermore, the edges of the garment may include, as along the inner surface along one edge, a segment of hook or pile fastener, such as fabricated from Velcro, as can be seen at 14, while the opposite edge, as at 15, upon its undersurface, may include the other segment of Velcro, as at 16, for securement with the defined edge 14, and allow for the garment, when wrapped, to snugly embrace the limb of the wearer, during treatment. Obviously, other types of fasteners can be utilized, such as clasps, one or more buckles, or any other type of means for securement of the edges of the garment together when wrapped around the limb of the patient.

In addition, any type of pump means, such as a bellows device, or bulb (not shown), or the like, may be applied to the valves 10, and facilitate the pumping of pressurized air into the garment, after installation, and in preparing it for treatment. Likewise, any type of release valve, incorporated into the structure of the valves 10, and which may be manipulated, to allow for discharge of air, will be applied thereto, in order to allow the patient to deflate the garment, and remove it, after treatment. These types of valves are readily known in the art, and are available for this type of adoption, installation, and usage.

Figures 5, 6, 8:
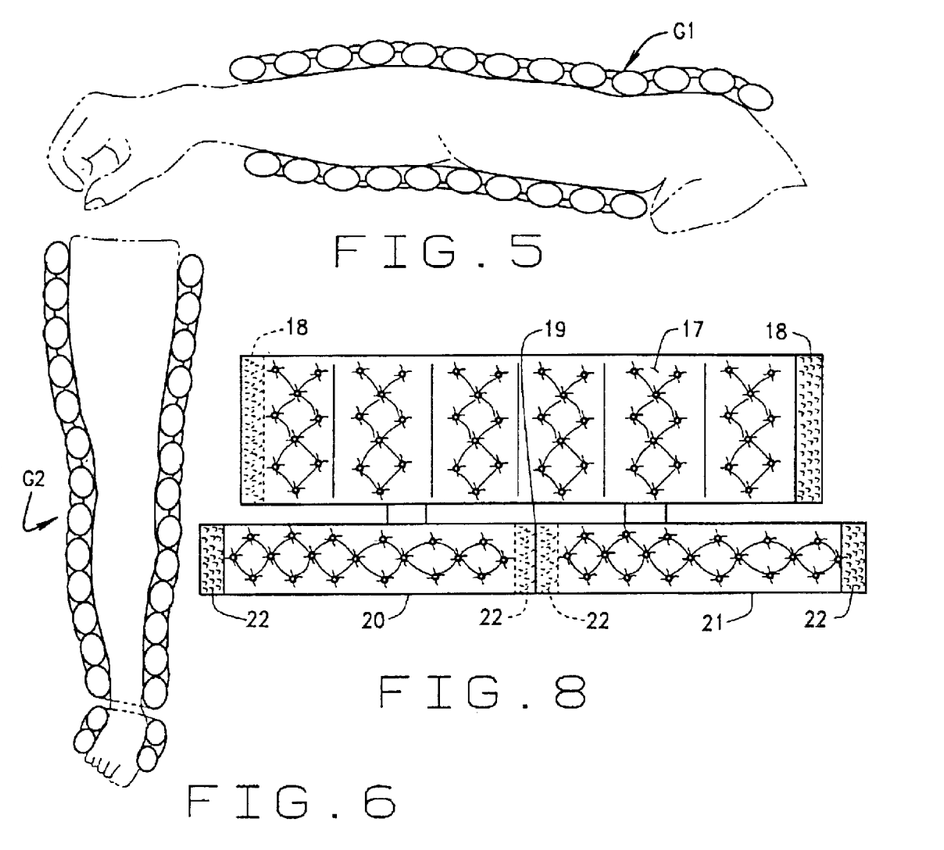
FIG. 5 is a view of a modified form of garment, that extends up to and onto the shoulder of the patient, from the vicinity of the wrist, for applying selective and controlled pressure along the length of the arm, to treat edema.
FIG. 6 is a view of the application of a modified garment to the thigh, leg, and ankle of the patient.
FIG. 8 is a plan view, or open view, of the modified garment shown in FIG. 7.

As can be seen in FIG. 5, the garment G1 is modified, and will extend from the wrist of the patient, up to and over the shoulder, to allow treatment along the extent of the shown limb, as can be understood.

Figure 7:
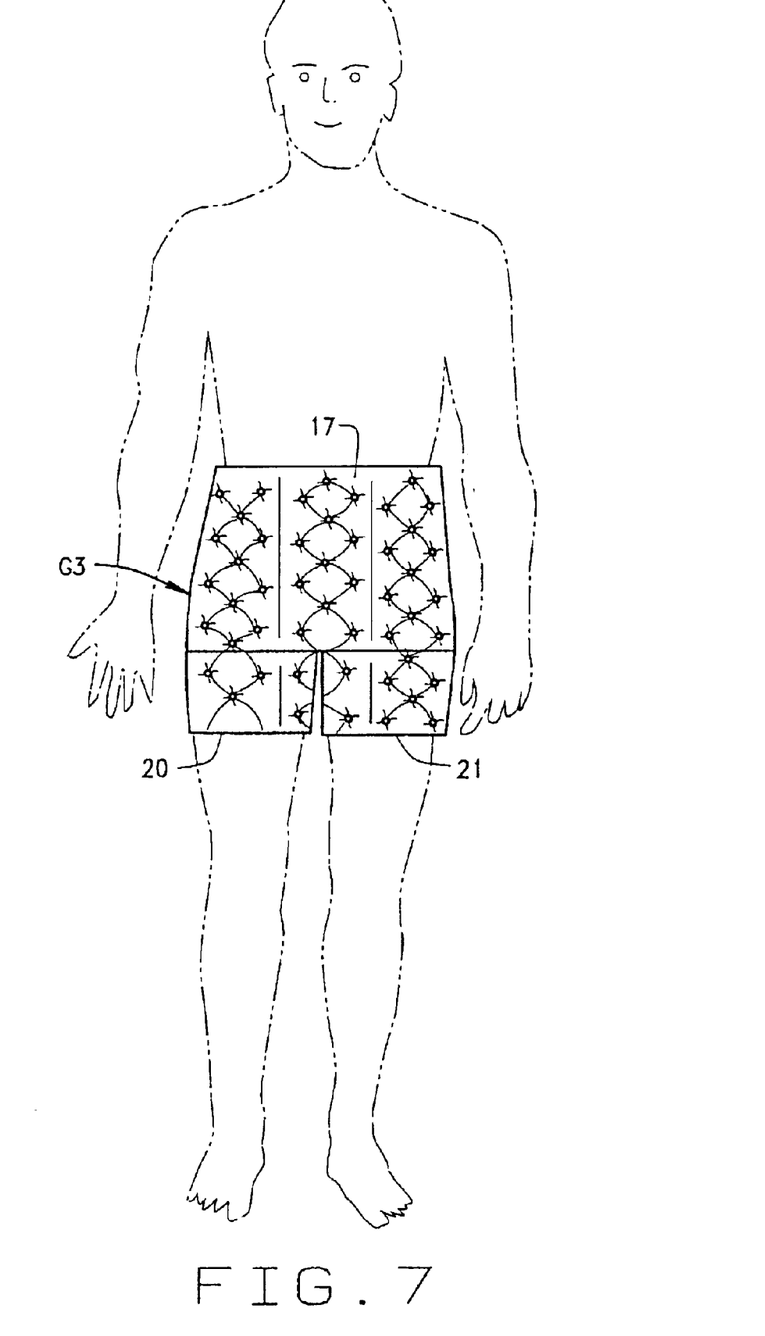
FIG. 7 is a view of a modified garment of the type that is applied at the vicinity of abdomen and upper thigh of the patient to provide edema treating pressure at these vicinities of the body.

In addition, as can be seen in FIG. 6, the Garment G2 may be further modified, and extend from the thigh, all the way down to the ankle, and even wrap about the foot, and readily available for inflation, to function to treat edema, that may be caused at these locations. Or, the leg wrap may extend simply down the calf, and embrace the ankle, and foot, as an alternative. Furthermore, as can be seen in FIG. 7, the garment G3 may be applied to the abdomen, waist, and upper thighs of the patient, for treatment of edema thereat. As noted in FIG. 8, this style of garment will have a waist embracing portion 17, with the usual fasteners 18, as previously explained, applied to either end, and in addition, will link by means of an appendage 19 to the upper thigh embracing components 20 and 21, which also include their various fastening means 22, about the upper leg of the patient. Nevertheless, and regardless what shape or configuration the garment undertakes, in its assembly and manufacture, it will include various upper and lower layers of material, that are hermetically sealed, and which include a series of grommets or other means for fastening of the layers of material together, to form those isolated pillows or segments to form pocketed pressurized air, for treatment of the affected limb, when applied. In addition, and while the terminology grommet has been used herein as means forming these pockets, obviously, these could be simply seal points, that connect the two layers of material together, regardless whether they include the apertures 11 therethrough, as previously explained for preferred embodiment.

As previously reviewed, the essence of this invention is to provide for a lightweight and washable type of garment, that can be applied to various affected limbs, even by the patient, himself/herself, to attain treatment, as required, or prescribed. It provides for controlled application of pressure, at various points along the treated area, in a manner that does not disrupt the desired and normal biological function of the vascular and lymph systems of the body, particularly at the treated area.

In addition, the garment is relatively small, flexible, is very compact for folding, easy to take when traveling, so that treatment can be undertaken anywhere, and not just at the hospital, medical facility, or the doctor's office. It can be done at home, or even on a business trip, as necessary. The garment has sufficient flexion, so that the limb, to which it is applied, can still be used, or manipulated, even during treatment.

Figure 9:
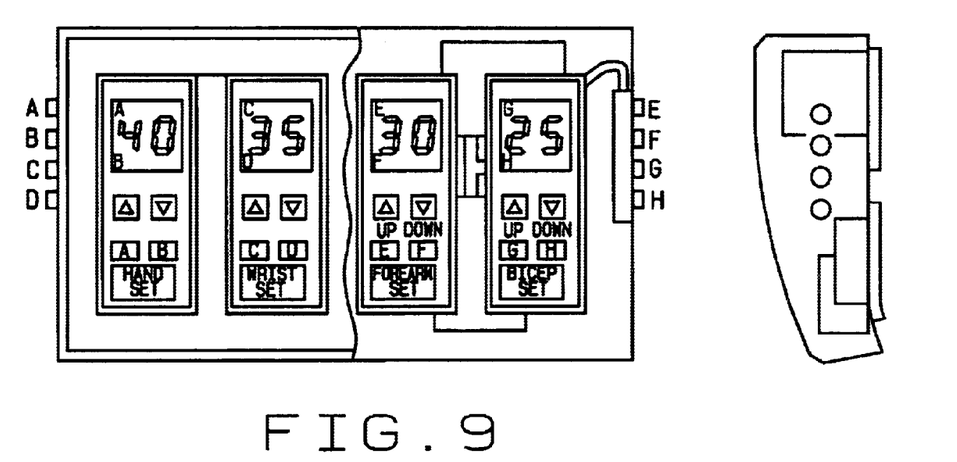
FIG. 9 is a schematic view of the front face of the electronic controller that is used for regulating the quantity of pressure added to or removed from various segments of the sleeve, during its usage.

FIG. 9 discloses the electronic controller, or at least provides a schematic of its front face, showing how various pressures are detected, determined, and used to automatically adjust the amount of air pressure pumped into the various segments of the sleeve, during its operations. Advancements in electronic circuit miniaturization now make it possible to develop a device that can control these pressures, be battery or otherwise operated, they are light weight, add significant safety features and allow for an individual complete freedom to move about and continue in their normal daily routine or sleep in complete comfort. The electronic controller automatically monitors the pressure at each section of the sleeve and verifies that it is set correctly. If, in the case of an arm sleeve, the patient should bend the arm, the sleeve would increase pressure in that section, and the controller would automatically vent that section of the sleeve back to its set point. When the patient straightens the arm, the pressure would reduce and the miniature pump inside the controller would automatically increase the pressure to the original set point.

Figure 10:
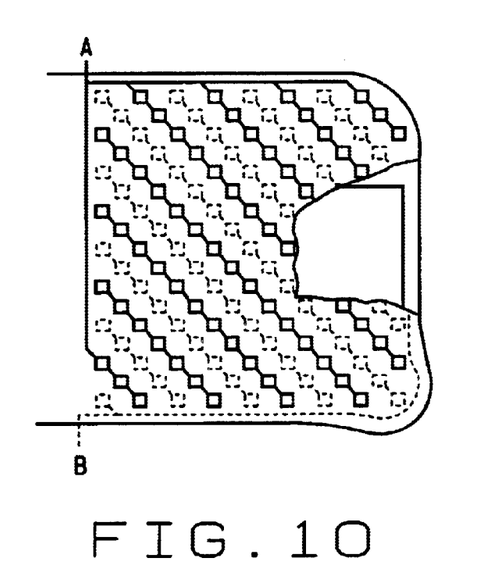
FIG. 10 provides a sectional view of the hand section of the sleeve, showing the various raised air pockets, the circuit lines leading to select of the air sections of the sleeve, which provide for a sensing as to where pressurized air must be added, or subtracted, in order to equalize the pressure of the sleeve upon the limb being treated.

As can be noted in FIG. 10, there are circuit leads that have sensors that are responsive to the amount of pressure at the various segments of air pockets, and can determine when pressure is becoming excessive and thereby should be reduced, or when pressure is lightening, and therefore, air should be supplied and pumped to the pocket to add pressure at select locations. This controller has several additional significant uses when used in conjunction with this sleeve devise. One, the pressures can be adjusted periodically on a prescribed time table to dynamically work the skin surface.

Secondly, the advance designs of the sleeve could incorporate twin bubble cell circuits in each section so that a constant alternating pressure in each cell circuit would result in a therapeutic massage of the afflicted area resulting in a potentially greater overall fluid reduction.

Figure 11:
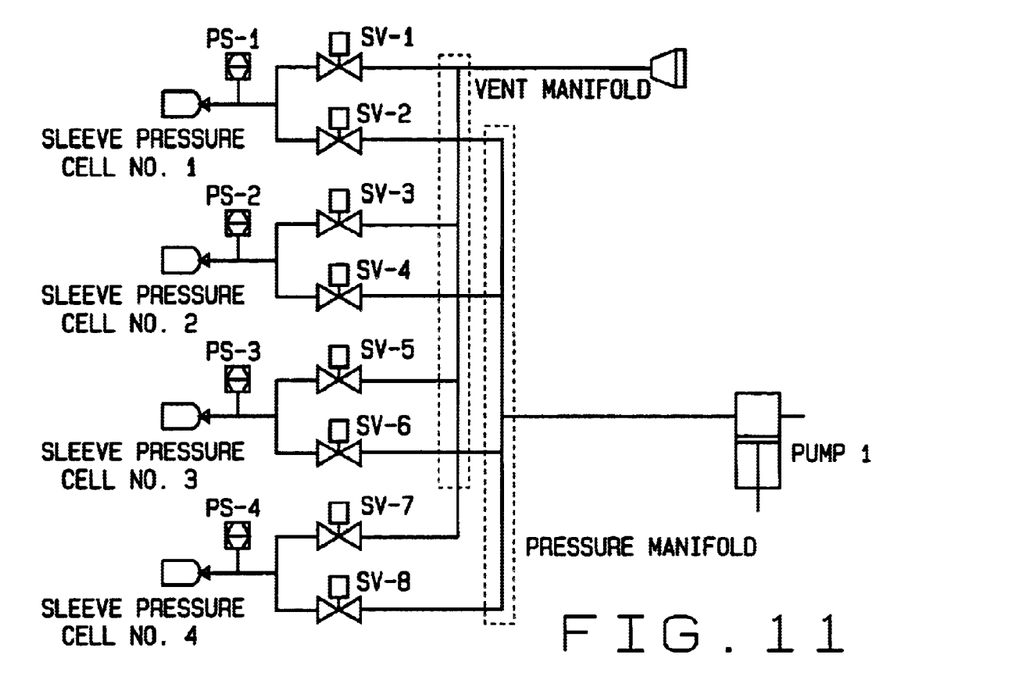
FIG. 11 provides a sleeve pneumatic schematic.

FIG. 11 discloses the lymphedema sleeve and the pneumatic schematic for the compression garment of this invention. As disclosed, the system is composed of a single DC powered air pump, as noted at pump 1, and includes eight solenoid valves, as noted. Each of the four compression cells, of the preferred garment, is continuously connected by way of tubing to a dedicated pressure transducer, generally identified as PS-1 through PS-4. The pump is connected to a manifold, which feeds each cell via a dedicated solenoid valve, as noted. Each compression cell is provided with a dedicated solenoid valve for venting its particular cell.

The system is capable of independently pressurizing and venting each compression cell. Variable pressure set points can be independently set for each cell. Fill rates will be impacted by set point pressure and the number of cells that are to be filled. The unit is capable of simultaneously pressurizing a cell(s) while venting another cell(s). Custom pressurization and massage can be implemented. The system will be able to quickly reduce pressure to ease bending the sleeve at the knee/elbow joint.

This system is capable of simultaneously performing in a desired operation, such as pressurization, static, or venting, on each of its separate compression cells.

Because of the necessity, in the event that the compression garment is designed incorporating four cells, of including eight solenoid valves within the structure, the cells and the garment will require a little more size, in order to accommodate such componentry.

Figure 12:
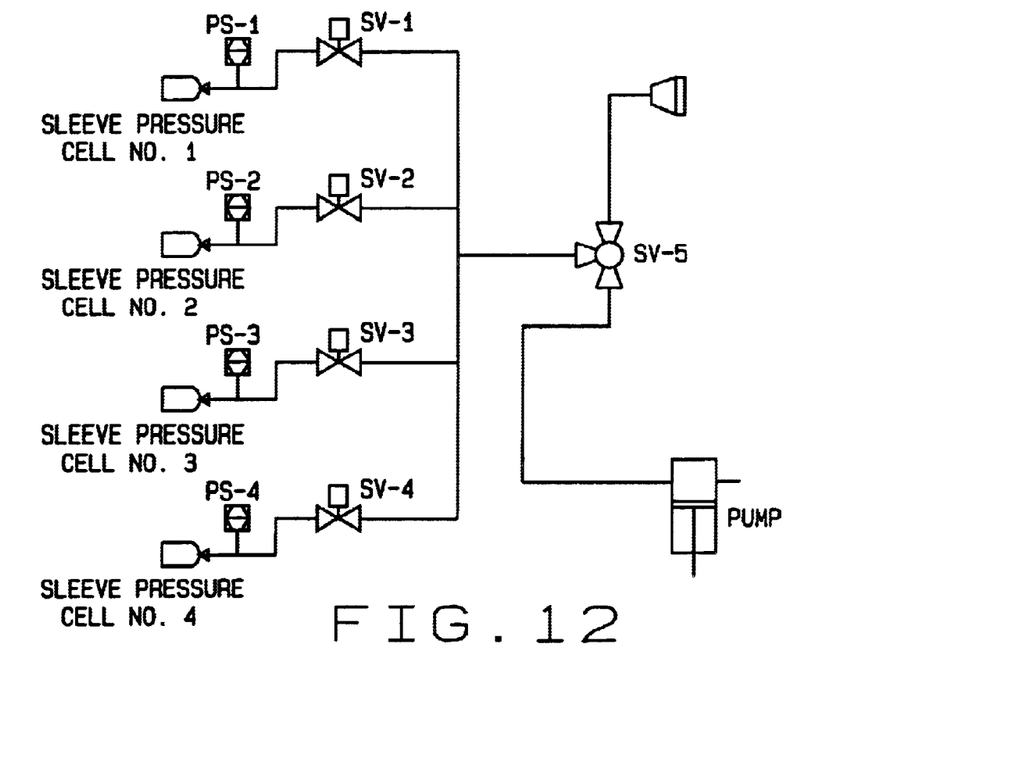
FIG. 12 provides a further modification to the sleeve pneumatic schematic.

On the other hand, the modification for the lymphedema sleeve pneumatic schematic as shown in FIG. 12 reduces the number of solenoid valves used. This system is composed of a single DC powered air pump and five solenoid valves. Each of the four compression cells is continuously connected via tubing to a dedicated pressure transducer. Each compression cell is provided with a dedicated solenoid valve for controlling the pneumatic access to the cell. A common manifold connects each cell control solenoid valve with the common port of a 3-way solenoid valve, as noted at SV-5. The normally open port of the 3-way valve is connected to the pump, and the normally closed port is connected to vent, as noted.

The system is capable of independently pressurizing or venting a specific compression cell. The unit will not be capable of simultaneously pressurizing a cell(s) while venting another cell(s). Variable pressure set points can be independently set for each cell. The fill rate will be impacted by set point pressure and the number of cells that are being filled. Custom pressurization and massage profiles are possible, but they will be limited by the inability to pressurize a cell while simultaneously venting another cell. The system will be able to reduce pressure to ease bending the sleeve at the knee/elbow joint, but the response time will be slower than the schematic as shown in FIG. 11.

The benefits of this particular system is that it is capable of performing any desired operation, i.e. pressurization, static, or vent, on each compression cell. The limitation of this particular system is that it can simultaneously fill or vent one or multiple cells. But, it can not do so at the same time. As a result, the system may have a desired state delayed until completion of the current cycle or state.

Figure 13:
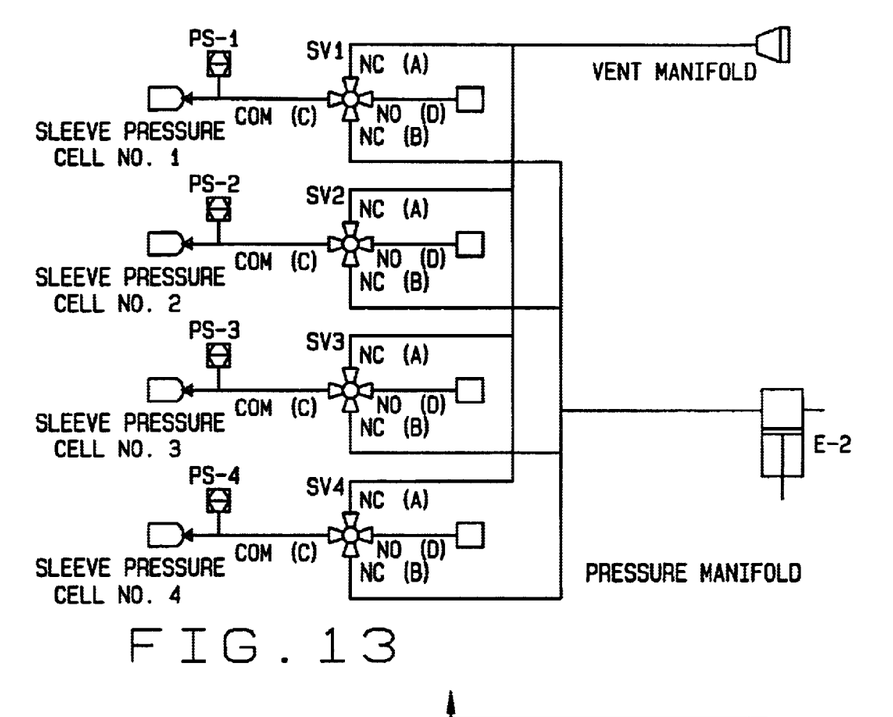
FIG. 13 provides a modification to the sleeve pneumatic schematic.

A further modification to the subject matter of this invention is shown in the system disclosed in the schematic of FIG. 13. This system is composed of a single DC powered air pump and four solenoid valves. Each of the four compression cells is continuously connected via tubing to a dedicated pressure transducer. Each compression cell is provided with a dedicated 3-position solenoid valve for controlling pneumatic access to the cell. The solenoid valve is comprised of two solenoids in three positions. The port position C is the common connection. Port A is a normally closed port that is connected to the common port C when the signal is applied to solenoid A. Port B is a normally closed port that is connected to the common port C when a signal is applied to solenoid B. Port D is the normally open port that is connected to port C when no signal is applied to solenoid A or B. Port C of the valve is capped. Port A is connected to the vent manifold. Port B is connected to the pump manifold. Each cell can be independently connected to the vent manifold, the pump manifold, or closed off.

This system is capable of independently pressurizing or venting a specific compression cell. Variable pressure set points can be independently set for each cell. Fill rate will be impacted by set point pressure and the number of cells that are being filled. Custom pressurization and massage profiles are possible. The system will be able to reduce pressure to ease bending the sleeve at the knee/elbow joint, and response time will be similar to the design option as set forth in FIG. 11.

This system is capable of performing any desired operation, such as pressurization, static, or vent, on each compression cell.

Figure 14:
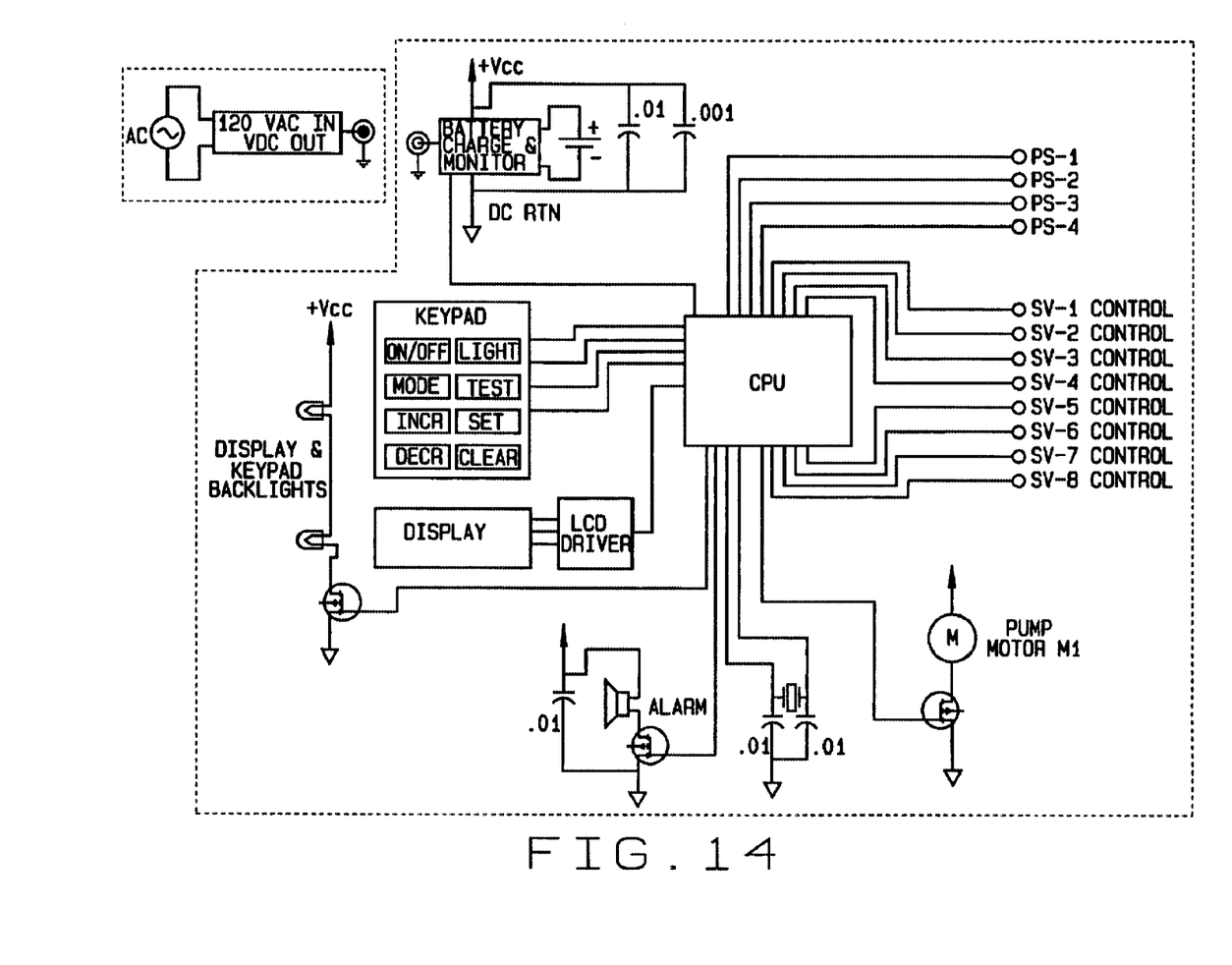
FIG. 14 provides a schematic of the electrical circuitry and the microprocessor controller and monitors for the compression garment of this invention.

Electrical schematic for operation of the electrical-pneumatic and solenoid controlled valves for the compression garment of this invention is shown in FIG. 14. As noted, power of the system is capable of operation from a rechargeable battery source, or DC power, provided by a standard 120 VAC volt wall adapter. The control includes the battery charge circuitry and battery state monitoring circuitry. The monitoring circuitry includes an alarm output to the microprocessor controller.

The display, as noted, is a backlit LCD display that provides control setting and operating parameter information to the user. The keypad, as noted, is a sealed multi-switch keypad which provides operator interface with the unit. The alarm, as also noted, is a Pizeo-electric audio alarm that provides audio indication of controller faults. The faults will include the low battery, cell over pressured/under pressured, pump fault and pressure sensor fault.

The pump is a DC powered pneumatic pump that provides pressurized air to the compression cells. The pump is controlled by a digital signal from the microprocessor, or CPU. The manufacturer of the CPU being Motorola, Inc. of Austin, Tex., Model No. 68HC16, or the manufacturer may be Microchip Technologies, Inc. of Chandler, Ariz., model No. PIC8F4320. The microprocessor sends a signal to a FET transistor that provides low side switch control of the pump motor.

The solenoid valves, generally identified at SV-1 through SV-8, are used to control the pressurization and venting of the compression cells, for the garment. The valves are controlled by a digital signal from the microprocessor to a FET transistor that provides low side switch control of the valve solenoid. Solenoid valves are bio compensated to minimize the effects of switching transients.

The pressure sensors, as indicated at PS-1 through PS-4, provide a temperature compensated DC signal to the controller microprocessor. The system includes a sensor for each compression cell. The sensors can be mounted on the sleeves or internal to the control unit.

Figure 15:
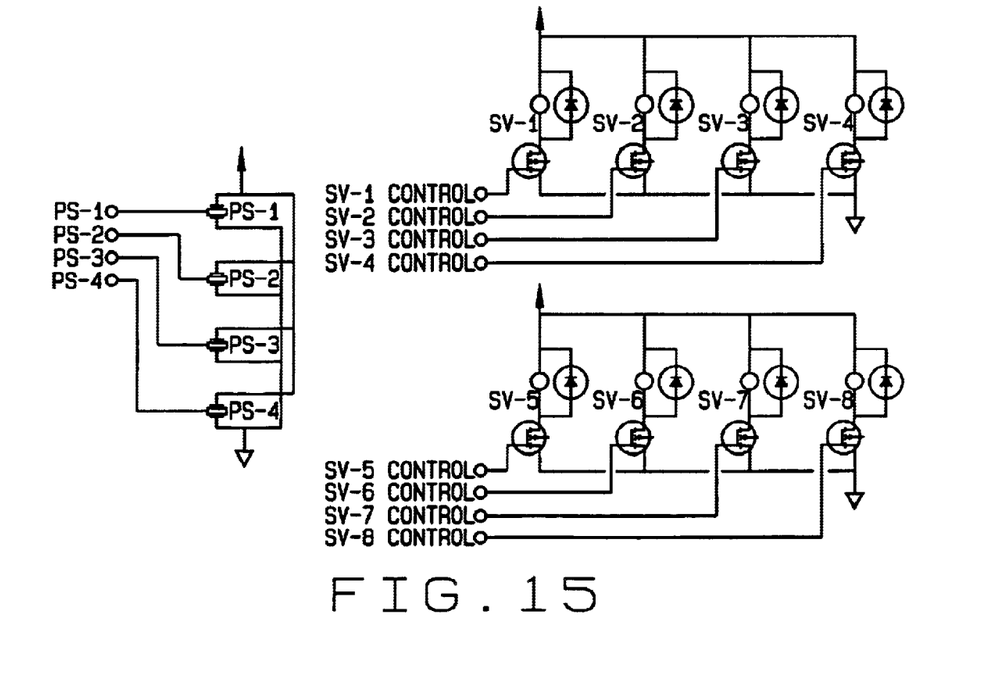
FIG. 15 is a further schematic of the circuitry used for the solenoid valves controlling the pneumatics for this compression garment.

The various FET transistors, and their association with the various valve solenoids, SV-1 through SV-8, can be seen in FIG. 15. In addition, the operations of the pressure sensors PS-1 through PS-4 can also be seen from this figure.

In the system operation, a microprocessor controller monitors the inputs from the keypad, the battery charger and monitoring circuits and the cell pressure sensors.

The serial data output from the microprocessor is used to send data to the LCD driver that displays operator information on the LCD. The display is activated in response to an operator input on the keypad, and any alarm condition or system failure. The LCD and keypad are backlit in response to a signal from the "light" button on the keypad. The backlighting remains on for a timed period and automatically turns off when no input from the keypad has been detected for a specified period.

Depending on pressure set point and the measured pressure from the pressure sensors, the electrically actuated solenoid valves are used to connect a cell to the pressure or vent manifold. Valve control signals from the microprocessor are connected to the gate input of a specified FET transistor. The FET provides low side switch control of the solenoid valves.

Prior to connecting a cell to the pressure manifold, the pump motor is turned on. The pump is controlled by a signal from the microprocessor that is connected to a FET transistor. The FET provides for low side switch control of the pump motor.

The system is designed to operate from a rechargeable battery. Separate circuitry provides for controlling the battery charge sequence and monitoring of the battery status. In the event of a low voltage condition, an alarm output is provided to the microprocessor. The system is capable of operating with a charged battery or with a 120 v AC charger attached to the controller.

An audio alarm is provided to indicate an unrecoverable out of tolerance condition. The frequency and pulse length of the alarm tone are specific to individual alarm conditions, such as low battery voltage, over/under pressure, sensor failure, etc.

Variations or modifications to the subject matter of this invention may occur to those skilled in the art upon reviewing the disclosure made herein. Such variations, if within the spirit of the desired results to be obtained from usage of this development, are intended to be encompassed within the scope of this invention as defined. The description of the preferred embodiment as set forth herein is done so for illustrative purposes only.

Having described the invention, what is claimed and desired to be secured by Letters Patent is:

1. A compression garment for application to various extremities of the body of a patient to provide for treatment of lymphedema and related forms of edema, said garment being formed having an upper layer and a lower layer of flexible material, of sufficient size and length to provide for covering of the extremity being treated, and having sufficient width to provide for its wraparound of the treated extremity, said upper and lower layers of flexible material being sealed together around their margins and intermediate thereof to provide various segments of internal pockets into which pressurized air may be injected during usage of the garment, there being a plurality of additional connections between the upper and lower layers of flexible material within each segment of internal pocket to form a plurality of further segment air pockets to provide for a plurality of pressure points within each segment of an internal pocket for exertion by the compression garment upon the extremity of the body being treated, pump means for supplying pressurized air to garment segment, valve means operatively associated with each segment of the garment, there being one valve means for each segment of internal pocket, to allow for injection of pressurized air into each segment of the garment during usage, a pressure sensor operatively associated with each segment of the garment, and provided for determining the amount of pressure maintained in each garment segment, and each valve means capable of being manipulated to provide for release of the pressurized air from each segment of the garment after completion of the treatment of lymphedema through usage of said compression garment, said plurality of segmented air pockets maintaing uniform distribution of pressurized air within each segment of an internal pocket during usage of said compression garment, electronic controller means operatively associated with each segment of the garment, and responsive to the measurements of each pressure sensor, to continuously determine the amount of pressure exerted by each segment of the garment, and said controller means in combination with each said pressure sensor selectively operating the addition of air from said pump means to select segment pockets, or initiating functioning of the valve means to discharge air from any segment of the garment, to provide for equalization of the pressure exerted by the garment in response to the location of the edema upon the extremity of the body being treated.

2. The compression garment of claim 1 wherein each valve means is a solenoid operated valve means.

3. The compression garment of claim 2 wherein each pressure sensor is a pressure transducer.

4. The compression garment of claim 3 wherein each of the plurality of additional connections forming the segmented air pockets within each segment of an internal pocket between the upper and lower layers of the flexible material forming the garment being formed as grommets.

5. The compression garment of claim 3 and including a vent operatively associated with the compression garment, a 3-way solenoid valve being in pressure communication between the pump, the vent, and the solenoid valves to regulate, in response to the measurements of the pressure sensors, the entrance or venting of pressurized air from within the select segments of the compression garment.

6. The compression garment of claim 3 wherein the solenoid valve operatively associated with each segment of the compression garment comprising 3-way solenoid valves.

7. The compression garment of claim 3 wherein the electronic controller means including a central processing unit for regulating and controlling the coordination of the pressure sensors, for determining when the readings of the pressure sensor provides for an actuation of its associated solenoid valve and either operations of the pump means or vent means, to provide for the admission or discharge of pressurized air from select of the garment segments.

8. The compression garment of claim 3 including a keypad for entrance of commands to the central processing unit for regulation of the operations of the compression garment, a display electrically connected to the central processing unit to provide for display of readings and data relative to measurements made by the pressure sensors, said pump means having an electrical connection to the central processing unit to provide for its initiation during the admission of pressurized air into select of the garment segments, the solenoid valves having electrical connection to the central processing unit for determining which of the valves are initiated for entrance of pressurized air to select garment segments, or for the discharge of air through the vent means to reduce the amount of pressurized air measured within select segments of the compression garment.

9. The compression garment of claim 8 and including an alarm means electrically connected to the central processing unit, and for detecting when high and low pressure readings are sensed by the pressure sensors for providing a warning pertaining to extreme levels of pressure in select segments of the compression garment.

10. The compression garment of claim 3, and including a battery means electrically connected to the central processing unit for providing electrical charge for operation of the solenoid valves, and the pressure sensors, to provide routine operations for the compression garment.

11. The compression garment of claim 1 and including a voltage regulator operatively connected to the central processing unit to provide for DC voltage for operations of the electrical systems operatively associated with the central processing unit of the compression garment.

12. The Compression garment of claim 3 and including a display means operatively associated with the central processing unit to display pressure readings detected by the pressure transducer.

13. The compression garment of claim 12 wherein the display includes a liquid crystal display.

14. The compression garment of claim 1 wherein each solenoid valve initiating the operations of a FET transistor, and said transistor providing for an initiation of the pump means for the delivery of pressurized air to its select garment segment.

15. The compression garment of claim 14 and including diode means electrically connected with each FET transistor for regulating the operations of each select solenoid valve.

* * * * *